(12) United States Patent
Egli

(10) Patent No.: US 10,045,883 B2
(45) Date of Patent: Aug. 14, 2018

(54) OPHTHALMIC SURGICAL DEVICE HANDLE AND ASSOCIATED DEVICES, SYSTEMS, AND METHODS

(71) Applicant: NOVARTIS AG, Basel (CH)

(72) Inventor: Lorenz Egli, Oberhallau (CH)

(73) Assignee: Novartis AG, Basel (CH)

( * ) Notice: Subject to any disclaimer, the term of this patent is extended or adjusted under 35 U.S.C. 154(b) by 341 days.

(21) Appl. No.: 14/866,401

(22) Filed: Sep. 25, 2015

(65) Prior Publication Data
US 2016/0324688 A1    Nov. 10, 2016

Related U.S. Application Data

(60) Provisional application No. 62/158,208, filed on May 7, 2015.

(51) Int. Cl.
*A61F 9/00*  (2006.01)
*A61F 9/007* (2006.01)

(52) U.S. Cl.
CPC .......... *A61F 9/00736* (2013.01); *A61F 9/007* (2013.01); *A61F 9/00709* (2013.01); *A61F 9/00763* (2013.01)

(58) Field of Classification Search
CPC .. A61F 9/00763; A61F 9/007; A61F 9/00709; A61F 9/00736; A61F 9/0079; A61M 1/0037; A61M 2210/0612; A61B 2017/00544; A61B 17/320016; A61B 17/3201
USPC ....... 606/107, 167, 169, 171; 604/22, 35, 43
See application file for complete search history.

(56) References Cited

U.S. PATENT DOCUMENTS

| 4,940,468 A | 7/1990 | Petillo |
| 5,314,440 A * | 5/1994 | Shapiro ............... A61B 17/3201 359/676 |
| 5,591,184 A | 1/1997 | Scott |
| 5,853,384 A | 12/1998 | Bair |
| 2009/0082715 A1* | 3/2009 | Charles ............... A61F 9/00763 604/22 |
| 2014/0171996 A1 | 6/2014 | Venkatesh |

FOREIGN PATENT DOCUMENTS

WO   2010124839 A1   11/2010

OTHER PUBLICATIONS

Alcon Vitreorentinol Product Catalog (2008).

* cited by examiner

*Primary Examiner* — Katherine M Shi
(74) *Attorney, Agent, or Firm* — Darien Reddick

(57) ABSTRACT

Systems, apparatuses, and methods of and for an ophthalmic surgical system are disclosed. An example ophthalmic surgical system may include a body sized and shaped for grasping by a user. The body may include a lumen and a vent in fluid communication with the lumen. The vent may be located and arranged to be selectively occluded, such as when a user places a finger over the vent, and selectively unoccluded, such as when the user removes the finger from over the vent. Fluid pressure within the lumen may be increased when the vent is occluded and decreased when the vent is unoccluded. A piston within the may be displaced in response to the fluid pressure changes within the lumen.

11 Claims, 10 Drawing Sheets

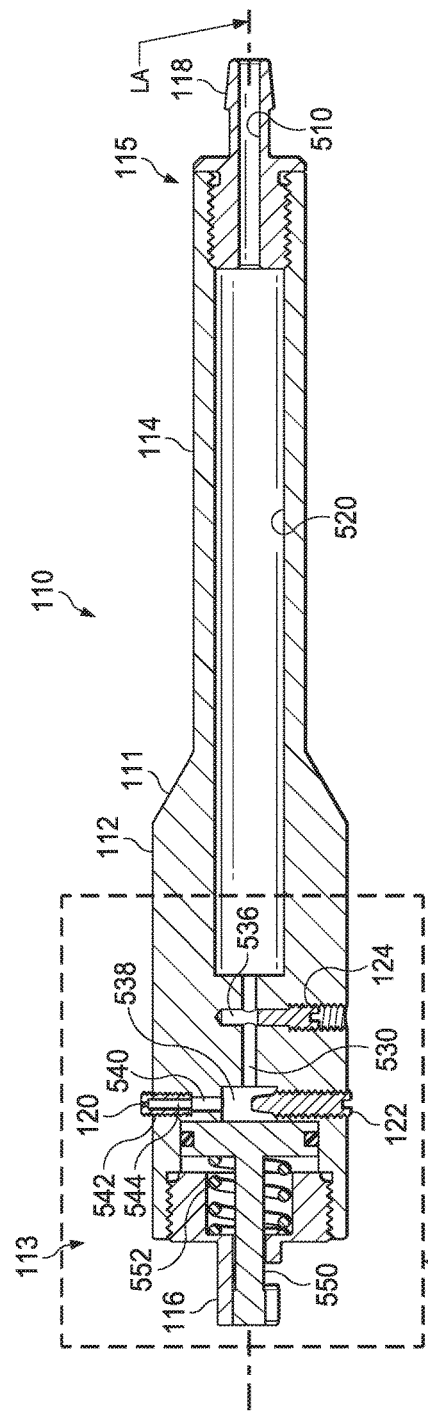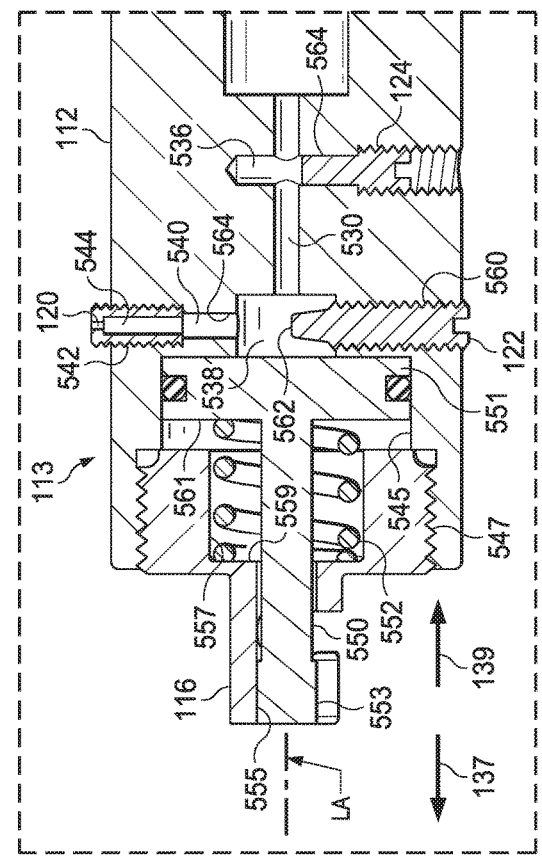
Fig. 5
Fig. 5A

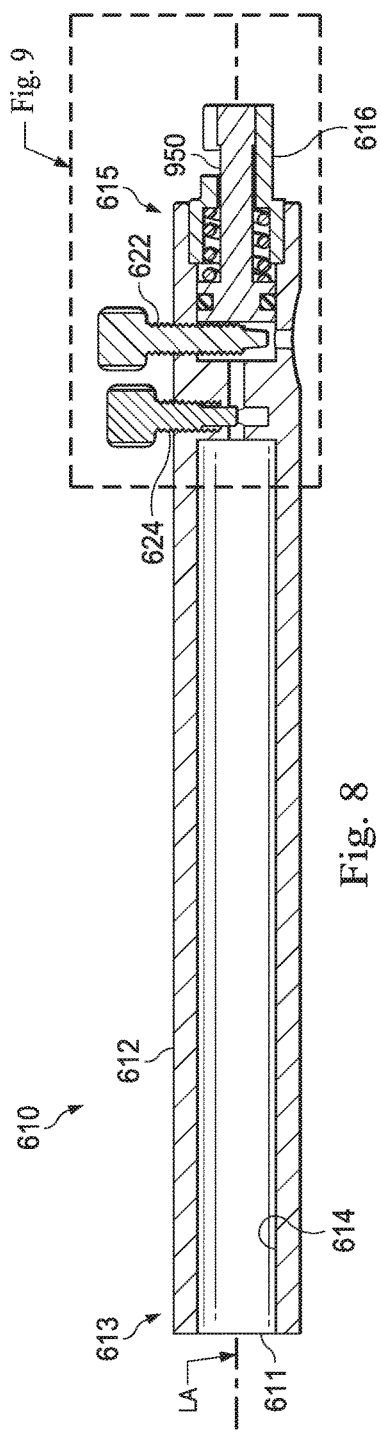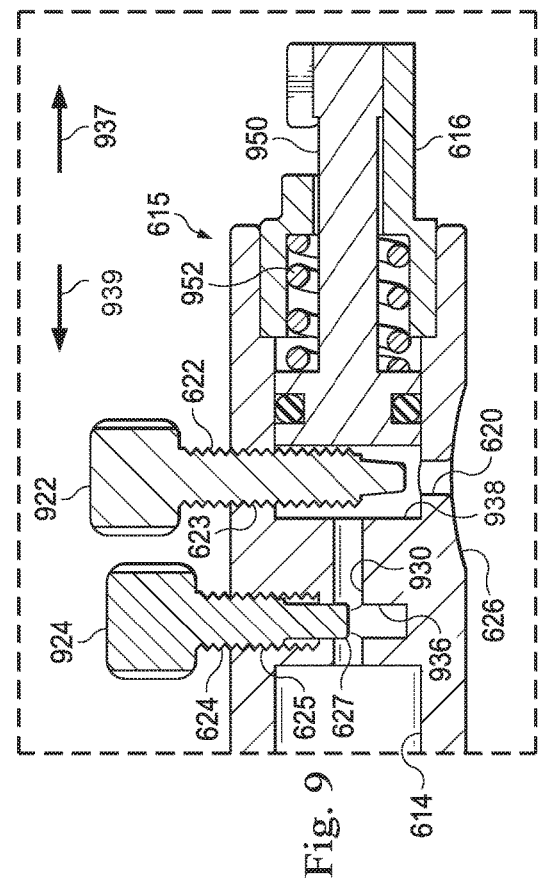

OPHTHALMIC SURGICAL DEVICE HANDLE AND ASSOCIATED DEVICES, SYSTEMS, AND METHODS

CROSS REFERENCE TO RELATED APPLICATIONS

This application claims the benefit of U.S. Provisional Application No. 62/158208, filed May 7, 2015, the contents of which are incorporated herein by reference.

TECHNICAL FIELD

The present disclosure is directed to ophthalmic surgical devices, systems, and methods. More particularly, but not by way of limitation, the present disclosure is directed to devices, systems, and methods of actuating an instrument tip by selectively changing fluid pressure within a device handle.

BACKGROUND

Microsurgical procedures frequently require precision cutting and/or removing of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. The cutting and removal of membranes may be particularly difficult in some delicate operations, such as mobile tissue management (e.g., cutting and removal of vitreous near a detached portion of the retina or a retinal tear) and vitreous base dissection.

Handheld surgical instruments, such as microsurgical forceps or scissors, may be used to cut and/or remove various body tissues. Generally, handheld instruments on the market are manually actuated. That is, the hand or fingers of a user, such as a surgeon or other medical professional, are pressed with force against a mechanism in the instrument handle to actuate the instrument tip.

During actuation, it is essential that the instrument tip remains stable near the target anatomy within the eye. Manual actuation is not ideal for surgeons because they can feel the friction and/or hysteresis of the actuation mechanism in their hands or fingers. Additionally, stick-slip effects or unintended, spontaneous movement of the instrument tip can occur. As a result, to achieve stable tip positioning, the surgeon must carefully coordinate actuation and positioning of the tip by filtering out the friction, hysteresis, and/or stick-slip effects, and by minimizing movement of the surgical device. Requiring that one or more fingers be pressed with force to actuate the instrument tip also has a negative influence on the precision of the surgical tasks, such as grasping or peeling of anatomy.

A pneumatic system is an alternative to the manually-actuated systems described above. In a pneumatic system, actuation of the instrument tip can be achieved, for example, via depression of a foot pedal. While this type of system solves some of the challenges above by removing actuating motion from the surgeon's hands, it still requires a level of coordination between hand and foot.

SUMMARY

According to one aspect, the present disclosure describes an ophthalmic surgical system including a body having a lumen formed in the body and configured to receive a pressurized fluid, and a vent providing fluid communication between the lumen and an exterior the body. The vent may be adapted to be selectively occluded to alter a pressure condition within the lumen between a pressurized condition and a nonpressurized condition.

Another aspect of the present disclosure is directed to an ophthalmic surgical system including a fluid source, an ophthalmic device handle, and an instrument tip. The ophthalmic device handle may include a body, a lumen formed in the body and in fluid communication with the fluid source, vent, and a piston. The vent may be formed in the body and provide fluid communication between the lumen and the exterior of the body. The vent may be adapted to be selectively occluded to alter a pressure condition within the lumen between a pressurized condition and a nonpressurized condition. The piston may be at least partially disposed within the body and moveable into an actuated position in response to the pressurized condition and to an unactuated position in response to the nonpressurized condition. The instrument tip may be coupled to the ophthalmic device handle. The instrument tip may be movable into an actuated configuration in response to movement of the piston to an actuated position and moveable into an unactuated configuration in response to movement of the piston to the unactuated position.

A third aspect of the disclosure is directed to method of performing an ophthalmic surgical procedure. The method may include grasping a handle of an ophthalmic surgical instrument. The ophthalmic surgical instrument may include a lumen and a vent providing fluid communication between the lumen and the exterior of the ophthalmic surgical instrument. The ophthalmic surgical instrument may be configured to permit continuous fluid flow through the lumen and out of the vent. The method may also include positioning an instrument tip of the ophthalmic surgical instrument near a tissue of the eye; occluding the vent to increase a fluid pressure within the lumen; and actuating the instrument tip to act on the tissue of the eye in response to the increase in fluid pressure within the lumen.

The various aspects of the disclosure may include one or more of the following features. A biasing element may be disposed within the body. The biasing element may be configured to bias the piston to the unactuated position. A first adjustment member may be configured to selectively increase and decrease a rate at which the piston returns to an unactuated position. An adjustment member may be configured to selectively increase and decrease a rate at which the piston moves to an actuated position. The adjustment member may be a threaded member received into a threaded bore formed in the body. The adjustment member may be movable in a direction perpendicular to a longitudinal axis of the body to selectively increase and decrease a rate at which is fluid pressure builds up within the body. An adjustment member may be configured to selectively increase and decrease a rate at which the piston is returns to an unactuated position. The adjustment member may be a threaded member received into a threaded bore formed in the body. The second adjustment member may be moveable within a chamber adjacent to the piston to selectively increase and decrease a rate at which fluid pressure within the chamber is relieved. A nozzle may be configured to be coupled to a fluid source. The body may have a substantially constant outer cylindrical shape. The body may include a plurality of sections. The plurality of sections may have different sizes. A connector may be disposed at a distal portion of the body. The connector may be configured to interface with a removable instrument tip.

The various aspects of the disclosure may also include one or more of the following features. The fluid source may be integrated into a surgical console. The instrument tip may be moved while the vent is occluded. The instrument tip may be returned to an unactuated position by unoccluding the vent. The instrument tip may be coupled to the handle. The surgical instrument may be coupled to a fluid source. A position of an adjustment member within the body may be altered to adjust a rate at which the instrument tip returns to an unactuated position. A position of an adjustment member within the body may be altered to adjust a rate at which the instrument tip is moved to an actuated position.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the systems, devices, and methods disclosed herein and together with the description, serve to explain the principles of the present disclosure.

FIG. 5 shows a cross-sectional view of the ophthalmic device handle of FIG. 3.

FIG. 5A shows a cross-sectional view of a portion of the ophthalmic device handle of FIG. 5.

FIG. 8 shows a cross-sectional view of the ophthalmic device handle of FIG. 6.

FIG. 9 shows a cross-sectional view of a portion of the ophthalmic device handle of FIG. 6.

Figure 1:
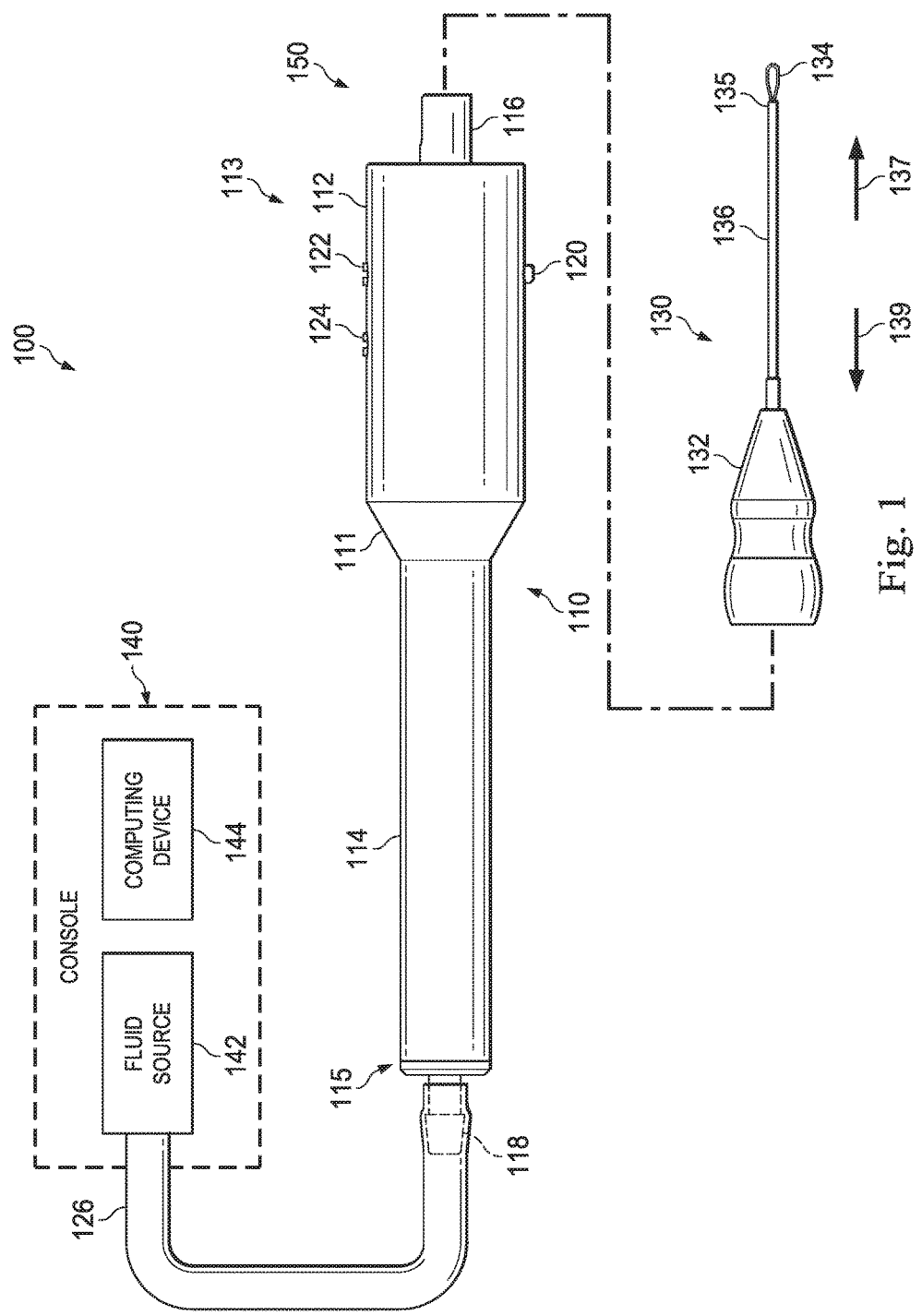
FIG. 1 is an illustration of an ophthalmic surgical system, including an example ophthalmic device handle.

These figures will be better understood by reference to the following Detailed Description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one or more implementations may be combined with the features, components, and/or steps described with respect to other implementations of the present disclosure. For simplicity, in some instances the same reference numbers are used throughout the drawings to refer to the same or like parts.

The present disclosure relates generally to devices, systems, and methods for actuating an instrument tip by varying the pressure within an ophthalmic device handle. The handle may include a lumen and a vent that provides fluid communication between the lumen and the outside environment. The handle may be connected to an air source or other fluid source that provides continuous fluid flow through the lumen and out of the vent. In some implementations, the air source may be a compressed air source to provide compressed air to the handle. A user, such as a surgeon or other medical professional, may occlude the vent by placing a finger over the vent. The pressure inside of the handle increases and actuates a piston that, in turn, actuates an instrument tip. When the user removes his or her finger from the vent, the fluid pressure inside the handle decreases, causing the piston and the instrument tip to return to an unactuated position.

The devices, systems, and methods of the present disclosure provide numerous advantages. Because mechanical actuation is replaced with fluid flow-based actuation, a user may focus less on compensating for friction, hysteresis, and/or stick-slip effects associated with mechanical actuation. Further, a user is able to use less force to close the fluid vent in the handle (compared to the force required to depress a lever or a handle for mechanical actuation). As a result, the precision for the surgical maneuvers, such as grasping or peeling anatomy, is increased. Additionally, a user is able to avoid actuating a separate device with another portion of his or her anatomy. For example, for instruments that may be actuated by manipulating a footswitch, the user is able to avoid coordinating hand and foot movements.

FIG. 1 illustrates an example ophthalmic surgical system 100. The system 100 may be used in various ophthalmic procedures, such as an anterior segment procedure, a posterior segment procedure, a vitreoretinal procedure, a vitrectomy procedure, a cataract procedure, and/or other desired procedures. The system 100 may include an ophthalmic device handle 110. The handle 110 may be sized and shaped for grasping by a user. The handle 110 may be made of any desired or suitable material, and may be formed by any method, including, for example, injection molding or machining. For example, the handle 110 may be made of a thermoplastic or metal. Also, a portion of the handle 110 may be textured or knurled to improve gripping.

Figure 2:
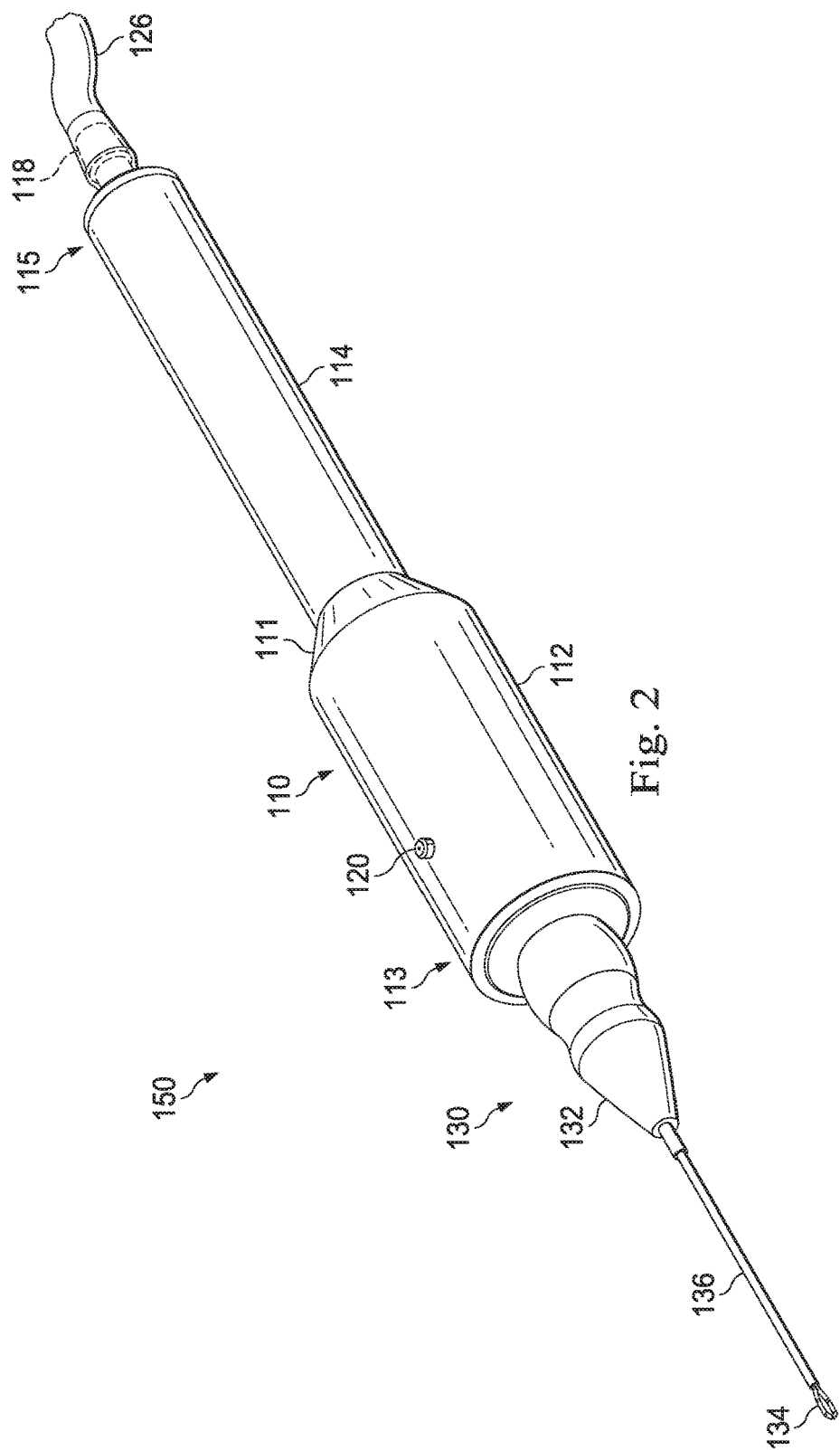
FIG. 2 is a perspective illustration of the example ophthalmic device handle of the ophthalmic surgical system of FIG. 1, coupled to an instrument tip.
Figure 3:
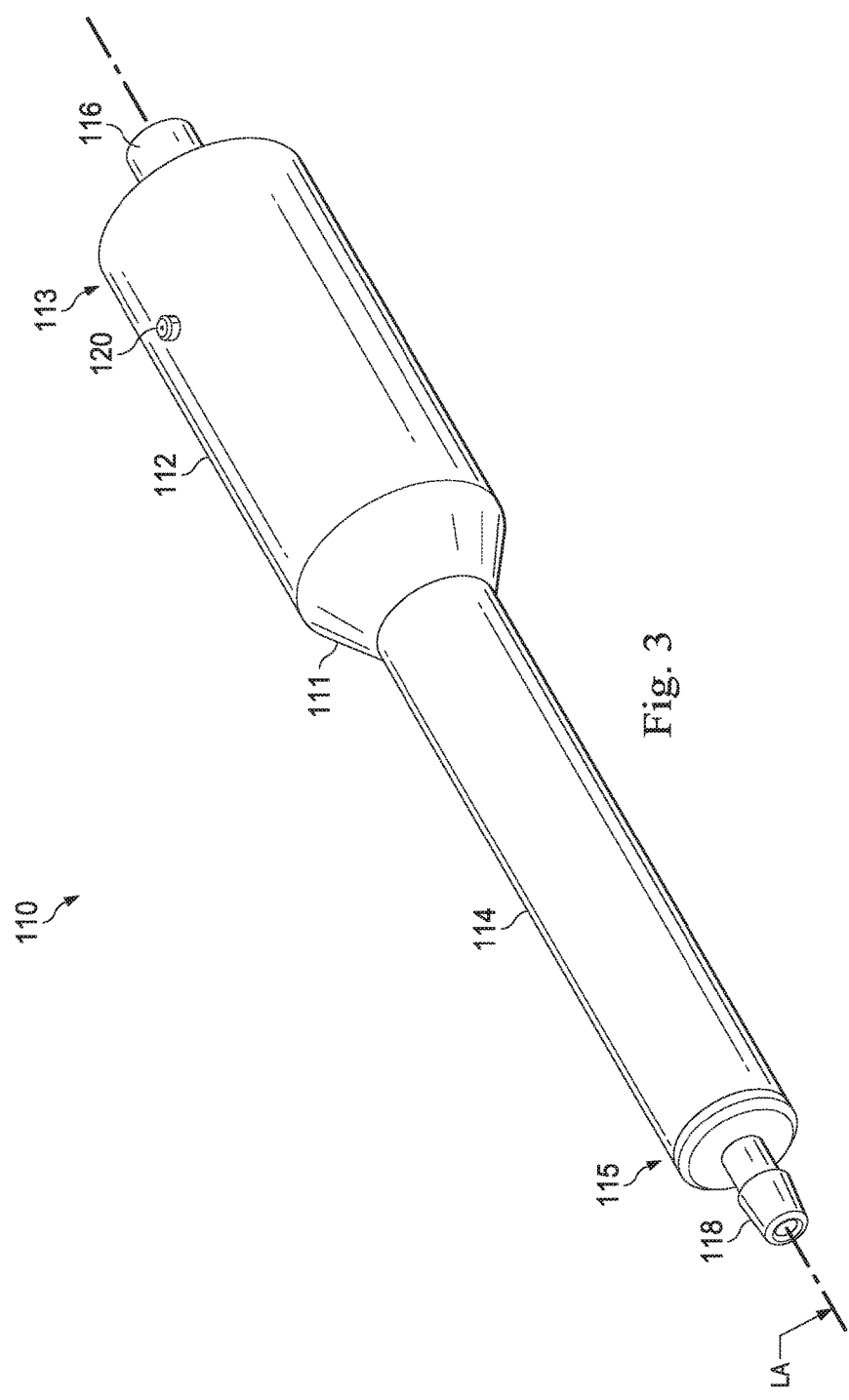
FIG. 3 is a perspective illustration of an example ophthalmic device handle showing the proximal end thereof.
Figure 4:
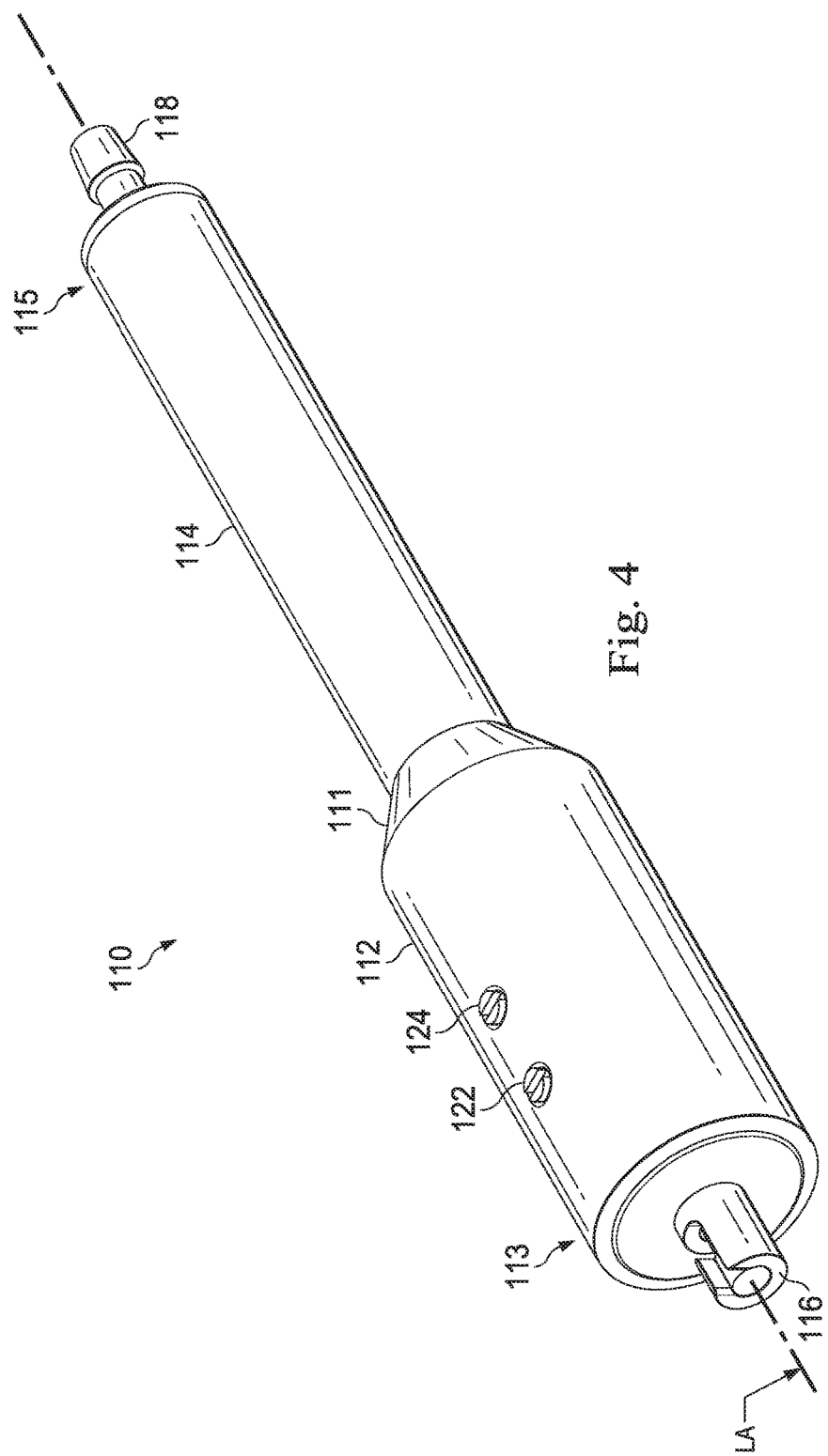
FIG. 4 is another perspective illustration of the ophthalmic device handle of FIG. 3 showing the distal end thereof.

Referring to FIGS. 1-5A, the handle 110 may include a body 111. FIG. 1 is a side view of the handle 110. FIGS. 2 and 4 are perspective views of the handle 110, with a distal portion 113 of the body 111 shown in the foreground. Relative to orientation of the handle 110 illustrated in FIG. 2, the handle 110 in FIG. 4 is rotated 180° about the longitudinal axis LA. FIG. 3 is a perspective view of the handle 110, with a proximal portion 115 shown of the body 111 in the foreground. FIG. 5 is a cross-sectional view of the handle 110, and FIG. 5A shows a portion of the handle 110 of FIG. 5.

The body 111 of the handle 110 may include sections 112 and 114. In the example shown, the sections 112 and 114 are cylindrically shaped. In other implementations, though, the sections 112 and 114 may have different shapes. In some instances, the sections 112 and 114 may have the same or similar shape. In other implementations, the section 112 and section 114 may have a different shape.

Although the example body 111 is shown as having two sections, in other implementations the body 111 may include fewer or additional sections. For example, in some instances, the body 111 may include a single section. In still other instances, the body 111 may include more than two sections. In the example body 111 shown, each of the sections 112, 114 has a different outer diameter. The distal section 112 has a larger diameter than the proximal section 114 so as to facilitate gripping by the user. In some instances, the outer diameter of the body 111 may be the same along substantially an entire length thereof. In still other instances, the body 111 may have more than two sections, each having a different diameter. In general, the body 111 may be sized and shaped in any manner that facilitates gripping by the user.

The system 100 includes an instrument tip 130 that is configured to be removably coupled to the handle 110. In FIG. 1, the handle 110 is decoupled from the instrument tip 130. FIG. 2 shows the handle 110 coupled to the instrument tip 130. The handle 110 includes a connector 116 at the distal portion 113 that mechanically interfaces with the instrument tip 130. The connector 116 and/or the instrument tip 130 may be variously sized and shaped in different implementations to facilitate the desired connection between the two components. In some instances, the instrument tip 130 may be single-use or disposable. In other instances the instrument tip 130 may be reusable. For example, in some instances, the instrument tip 130 may be reused after being sterilized.

In some instances, the handle 110 may be reusable. For example, in some instances, the handle 110 may be autoclavable and/or otherwise sterilizable. The handle 110 may be utilized in different surgical procedures. For example, different surgical procedures may require one or more instrument tips that are different from other surgical procedures. The handle 110 may be used in different surgical procedures requiring one or more different instruments by selecting and coupling an appropriate surgical tip to the handle 110. Further, different instrument tips may be coupled to the same handle 110 during the course of a single surgical procedure.

While implementations herein may refer to a removable instrument tip 130, it is understood that the handle 110 may be implemented with a non-removable and/or fixedly coupled instrument tip. Together, the handle 110 and the instrument tip 130 may be described as an ophthalmic surgical instrument 150.

The instrument tip 130 may be any surgical tool. For example, the instrument tip 130 may be forceps, scissors, and/or other desired instruments. The user may cut, tear, handle, and/or otherwise manipulate tissue at the surgical site using the instrument tip 130. While forceps are the particular instrument tip illustrated in FIGS. 1, 2, 11, and 12, it is understood that any suitable instrument tip may be utilized with the handle 110.

In the exemplary implementation of FIG. 1, the instrument tip 130 includes a body 132, an actuation tube 136, and jaws 134. The jaws 134 may be a portion of the instrument tip 130 that directly contacts the target surgical tissue, such as to cut, tear, handle, and/or manipulate the tissue. In some instances, the jaws 134 may be formed from stainless steel or titanium. However, other materials may also be used. For example, in some instances, the jaws 134 may be formed from a polymeric material, such as polypropylene. The scope of the disclosure is not so limited. Thus, other materials may be used to form the jaws 134. The jaws 134 protrude from a distal end of the tube 135. In some instances, the jaws 134 may be fixed relative to the body 132. The tube 135 may be slideable over and relative to the jaws 134 such that a distal end 135 of the actuation tube 136 engages the jaws 134 to selectively open and close the jaws 134. In other instances, the tube actuation 136 may be fixed relative to the body 132, and the jaws 134 may be slideable relative to the actuation tube 136, such that the jaws 134 engage the distal end 135 of the actuation tube 136 to selectively open and close the jaws 134.

The jaws 134 may include a stem that extends through the actuation tube 136. Proximal portions of an assembly including the jaws 134 may be disposed within the actuation tube 136 and the body 132. In some instances, the actuation tube 136 may be any suitable medical grade tubing, such as titanium, stainless steel, or suitable polymer. The actuation tube 136 and stem of the jaws 134 may be sized such that the actuation tube 136 and stem easily reciprocate relative to each other. In a surgical procedure in the posterior segment of the eye, for example, the actuation tube 136 may extend through the sclera into the globe of the eye, with the jaws 134 positioned proximate to the target surgical tissue.

The instrument tip 130 may be actuatable between at least two positions (e.g., an unactuated position, an actuated position, etc.). For example, when the instrument tip 130 is actuated, the actuation tube 136 may translate distally (i.e., in the direction of arrow 137) relative to the body 132, acting on and forcing the jaws 134 closer together toward a closed condition. When the instrument tip 130 returns to an unactuated position, the actuation tube 136 translates proximally (i.e., in the direction of arrow 139) relative to the body 132 such that the jaws 134 open.

In some implementations, the instrument tip 130 may be actuatable between more than two positions. For example, the instrument tip 130 may be actuatable to a closed configuration, an open configuration, and an intermediate configuration disposed between the open and closed configurations. In some implementations, the jaws 134 may be biased to be in a closed configuration such that actuating the instrument tip 130 causes the jaws 134 to open. In other implementations, the jaws 134 may be biased to be in an open configuration such that actuating the instrument tip 130 causes the jaws 134 to close. The instrument tip 130 may be actuated when a piston 550 of the handle 110 is actuated, as described in greater detail herein.

The system 100 may include a fluid source 142 in fluid communication with the handle 110. The fluid source 142 may be configured to output a fluid, such as any suitable liquid(s) and/or gas(es), to the handle 110. The fluid source 142 may be part of and/or otherwise in fluid communication with a fluidics cassette or fluidics subsystem of a surgical console 140. In other instances, the fluid source 142 may be separate from a surgical console. The fluid source 142 may include a reservoir of the fluid or a mechanism in fluid communication with such a reservoir. For example, the mechanism may be a pump, compressor, and/or component(s) of the fluidics subsystem configured to provide continuous fluid flow to the handle 110 as described herein.

In some implementations, the fluid source 142 may be an air source and may provide continuous air flow to and within the handle 110. As shown in FIG. 1, the fluid source 142 is integrated in the surgical console 140. As also explained, the fluid source 142 may be remote from the surgical console 140 in other implementations. Any suitable conduit configured to carry the fluid, such as the tube 126, may extend between the fluid source 142 and a nozzle 118 at the proximal portion 115 of the handle 110.

Referring to FIG. 5, fluid from the fluid source 142 may enter the handle 110 via the nozzle 118. A lumen 510 of nozzle 118 may be in fluid communication with a lumen 520 of the handle 110. In the example shown in FIG. 5, the nozzle 118 is a distinct component that is coupled to the body 111 of the handle 110 (such as during manufacturing, after being sterilized, prior to surgical use, etc.). For example, in some implementations, the nozzle 118 may be received into a bore of the body 111, such that an exterior threaded surface of the nozzle 118 matingly engages an interior threaded surface on the bore of the body 111. In other implementations, the nozzle 118 may be integrally formed with the body 111.

Referring again to FIG. 1, the fluid source 142 may be communicatively coupled to a computing device 144. The computing device 144 may include any desired processing circuit architecture, including a processor, memory, and/or other suitable components. The computing device 144 may generate and transmit control signals to the fluid source 142, such as to start fluid flow, stop fluid flow, increase a flow rate of the fluid, decrease a flow rate of the fluid, etc. The computing device 144 may be configured to monitor fluid pressure and/or other parameters at various points of the system 100 (e.g., output pressure of the fluid source 142, pressure within the handle 110, etc.) and generate control signals based thereon. The computing device 144 may also generate and transmit control signals in response to user inputs received via one or more user input devices communicatively coupled to the computing device 144. In the implementation of FIG. 1, the computing device 144 is integrated in the surgical console 140. In other instances, the fluid source 142 may be remote from a surgical console 140.

Referring to FIG. 5, the handle 110 includes the lumen 520. In the illustrated implementation, the lumen 520 has a constant diameter along its entire length. In other implementations, the diameter of the lumen 520 may vary along its length, including, for example, portions of larger or smaller diameters. Further, although the handle 110 and lumen 520 are shown as having a circular cross-section, the scope of the disclosure is not so limited. Rather, the handle 110 and/or lumen 152 may have any shape. For example, the lumen 520 may have any cylindrical shape. Further, the cylindrical shape of the lumen 520 may be constant along its length. In other instances, the size of the lumen 520 may vary along its length.

The lumen 520 permits fluid flow (e.g., gas flow, liquid flow, etc.) through the handle 110. For example, air, such as compressed air, may flow from the proximal portion 115 of the handle 110 towards the distal portion 113. The lumen 520 may extend along a substantial length of the handle 110. For example, the lumen 520 may extend between about 1% and about 99%, between about 30% and about 90%, between about 40% and about 90%, greater than 50%, and other desired proportions relative to the length of the handle 110.

Referring to FIGS. 5 and 5A, the lumen 520 may be in fluid communication with a vent 120 at the distal portion 113 of the handle 110. The vent 120 provides fluid communication between the lumen 520 and the exterior of the handle 110. In some instances, the vent 120 may be coupled to a conduit that directs the fluid away from the handle 110. Thus, fluid flowing through the lumen 520 may exit the handle 110 via the vent 120.

In the example shown in FIG. 5A, the vent 120 is defined as an opening formed in a fitting 542. The fitting 542 may include an external threaded surface that matingly engages a corresponding threaded surface formed on an interior of a bore 540. However, the fitting 542 may be removably or fixedly secured to the handle 110 in any desired manner. In some instances, the fitting 542 may protrude from an exterior surface of the handle 110. Because of this, a user may easily tactilely locate the vent 120 with his or her finger using a sense of touch. In some instances, a cross-sectional size of the vent 120 may be made small or otherwise minimized. A small cross-sectional size of the vent 120 allows a user to close the vent 120 with a lower force than may be required to close the vent 120 having a larger cross-sectional size.

The fitting 542 may be a distinct component that is coupled to the body 111. In other implementations, the fitting 542 may be eliminated, and a protrusion for the vent 120 may be integrally formed in the body 111. In still other implementations, the vent 120 may be an opening in the body 111 that is in fluid communication with the lumen 520.

As shown in FIGS. 1-5A, the vent 120 is disposed at the distal portion 113 of the handle 110. In other implementations, the vent 120 may be located at any desired location along the body 111. For example, the vent 120 may be located along a central portion or the proximal portion 115 of the handle 110. While the illustrated implementation includes a single vent 120, other implementations may include two or more vents that are proximate to or spaced from one another. In such implementations, the user may position two or more fingers over the respective two or more vents to control the instrument tip 130.

Referring again to FIGS. 5 and 5A, the lumen 520 is in fluid communication with lumen 530. Lumen 530 intersects bore 536 and chamber 538. Chamber 538 is in fluid communication with bore 540, a bore 544 of the fitting 542, and vent 120. Thus, fluid from fluid source 142 is permitted to enter the handle via nozzle 118; pass through lumens 510, 520, and 530; pass through bore 540 and bore 544; and pass out of the handle 110 through vent 120.

As shown in FIG. 5A, the handle 110 also includes a bore 545. The connector 116 may be received into the bore 545, such as by a mating threaded connection 547. A piston 550 having a piston head 551 and a piston stem 553 is disposed in the bore 545. The piston stem 553 of the piston 550 extends through a bore 555 formed in the connector 116. A biasing element 552 is received in an enlarged portion 557 of the bore 555 and is disposed between a flanged surface 559 of the bore 553 and a distal surface 561 of the piston head 551. In the illustrated example, the biasing element 552 is a coil spring. However, the scope of the disclosure is not so limited. Rather, the biasing element may be any suitable element operable to bias the piston 550 in a desired direction.

In use, fluid flows from the fluid source 142 to the handle 110 via the tube 126. Fluid enters the lumen 510 of the nozzle 118 and flows into the lumen 520, the lumen 530, the chamber 538, the bore 540, and the bore 544. When the vent 120 is unoccluded, the fluid then exits the handle 110 via the vent 120. Fluid may continuously flow through the lumen 520, from the proximal portion 115 towards the distal portion 113, and out of the vent 120 so long as the vent 120 is not occluded. The computing device 144 may provide a control signal to the fluid source 142 to provide a constant or variable output pressure, flow rate, etc., such that the fluid continuously flows within the handle 110. Fluid pressure within the handle 110 may remain the same when the vent 120 is not occluded, as the fluid continuously flows through the handle 110 and out of the vent 120. When the vent 120 is occluded, such as by being covered by a finger of a user, fluid pressure within the handle 110 increases. A user may fully or partially occlude the vent 120, resulting in a fluid pressure increase in the handle 110. A user may fully or partially occlude the vent 120 in order to control an amount of actuation of the piston 550. The handle 110 may be considered to be in a pressurized condition when the vent 120 is partially or fully occluded. The handle 110 may be considered to be in a nonpressurized condition when the vent 120 is unoccluded. The fluid pressure acts on the piston head 551 to displace the piston 550. At a level high enough to overcome the force exerted by the biasing element 552, the increased fluid pressure displaces the piston 550 distally in the direction of arrow 137. Movement of the piston 550 in the direction of arrow 137 causes actuation of an instrument tip. For example, in the context of instrument tip 130, displacement of the piston 550 distally may cause distal displacement of the actuation tube 136, resulting in closure of jaws 134. Therefore, by increasing the fluid pressure within the handle 110, a user may actuate the instrument tip 130, such as to grasp anatomy with the jaws 134, for example. When the vent 120 is unoccluded, the fluid pressure is permitted to vent from the handle 110 via the vent 120. In response to the decreased fluid pressure, the biasing element 552 expands and displaces the piston 550 proximally in the direction of arrow 139. As a result, the instrument tip 130 is moved back to an unactuated position. Thus, in the example shown, the jaws 134 are returned to an open position.

While the example handle 550 is configured to cause the piston 550 to move distally when fluid pressure increases within chamber 538, other implementations may function differently. For example, in other instances, the handle 110 may be configured such that, when fluid pressure within the chamber 538 increases, the piston 550 is made to be displaced proximally in the direction of arrow 139, and a decrease in fluid pressure within chamber 538 results in distal displacement of the piston 550 in the direction of arrow 137. Although the example handle 110 shown in FIGS. 5 and 5A is actuated by linear translation of the piston 550, the scope of the application is not so limited. Rather, in other implementations, the piston 550 may rotate, pivot, and/or otherwise move when actuated.

The user may keep his or her finger over the vent 120 so long as the user desires to keep instrument tip 130 (e.g., the jaws 134) in the actuated position. For example, the vent 120 may be covered while the user grasps and moves anatomy. When the vent 120 is opened after being occluded, such as when the user removes his finger from the vent 120, fluid pressure inside of the handle 110 decreases and the instrument tip 130 returns to an unactuated position. For example, as the fluid pressure decreases, the force of fluid (e.g., within the chamber 538) acting on the biasing element 552 is no longer sufficient to overcome the force of the biasing element 552. The biasing element 552 urges the piston 550 such that the piston 550 is translated proximally to an unactuated position. For example, the user may remove his or her finger from the vent 120 to release anatomy from the jaws 134.

A handle within the scope of the disclosure may also include adjustment members. For example, the handle 110 includes adjustment members 122 and 124 that control fluid flow within the handle 110. The adjustment members 122 and 124 are disposed at the distal portion 113 of the body 111. In some instances, the adjustment members 122 and 124 may be disposed on an opposing side of the vent 120. However, the adjustment members 122 and/or 124 may be located at any radial position relative to longitudinal axis LA. The position of the adjustment members 122 and 124 may determine the velocity (or rate) at which the instrument tip 130 moves to an actuated position and moves back to an unactuated position.

The adjustment member 124 is configured to selectively increase and decrease the rate at which the piston 550 and the instrument tip 130 moves to an actuated position. Generally, the adjustment member 124 may be variously sized and shaped to selectively increase and decrease the rate at which fluid pressure within the chamber 538 builds up. The adjustment member 124 may be a screw or other threaded component received in bore 564. In the illustrated implementation, the adjustment member 124 is movable in a direction perpendicular to the longitudinal axis LA of the body 111. In other implementations, the adjustment member 124 may be disposed in other orientations relative to the longitudinal axis LA. As shown, for example, the adjustment member 124 may be movable in a direction transverse to the lumen 520. In general, the adjustment member 124 may be movable in a direction transverse to any fluid passageway (e.g., the lumen 510, the lumen 520, the lumen 530, etc.) within the handle 110. The user may position the adjustment member 124 such that a portion, all, or none of the adjustment member 124 occludes the fluid passageway.

Referring to FIG. 5A, the adjustment member 124 may be positioned such that the adjustment member 124 fully occludes lumen 530; positioned such that no part of the adjustment member 124 occludes lumen 530; or positioned anywhere in between. When the adjustment member 124 completely occludes the lumen 530, a distal end of the adjustment member 124 is received within the bore 536. As the adjustment member 124 is moved farther into lumen 530, the cross-sectional area of the lumen 530 is reduced. Thus, the adjustment member 124 creates an obstruction to the fluid flowing through the handle 110. The result is such that the fluid entering the handle via the lumen 510 of the nozzle 118 must flow around the adjustment member 124. Accordingly, the fluid pressure proximal to (e.g., in the direction of the arrow 139) the adjustment member 124 is greater than the fluid pressure distal to (e.g., in the direction of the arrow 137) the adjustment member 124. When the vent 120 is occluded, such as when the user's finger is positioned on the vent 120, the decreased fluid pressure on the distal side of the adjustment member 124 also results in relatively longer time period for the fluid pressure in the chamber 538 to build up and actuate the piston 550. Thus, the farther the adjustment member 124 extends across the lumen 530, the slower the rate at which the piston 550 is actuated. In contrast, when the adjustment member 124 occludes the lumen 530 to a lesser extent (or not at all), there is less of an obstruction (or no obstruction) to fluid flow. Thus, the fluid pressure on the proximal side of the adjustment member 124 may be higher than the fluid pressure on the distal side of the adjustment member 124 by a relatively smaller amount (or the fluid pressures on the proximal and distal sides may be equal). Thus, the fluid pressure within the chamber 538 builds up at a relatively faster rate and the piston 550 is correspondingly actuated at a relatively faster rate.

The adjustment member 122 may be configured to selectively increase and decrease the rate at which the piston 550 and the instrument tip 130 returns to an unactuated position. Generally, the adjustment member 122 may be variously sized and shaped to selectively increase or decrease the rate at which pressure within the handle 110 is relieved, such as by limiting a cross-sectional area of the vent 120 and thereby decreasing the fluid flow rate out of the vent 120. For example, the adjustment member 122 may be a screw or other threaded component received within bore 560. The bore 560 is in fluid communication with chamber 538. The chamber 538 is adjacent to the piston 550 and is in fluid communication with the lumen 530 and the vent 120. In the illustrated implementation, the adjustment member 122 is movable within the chamber 538. The user may position the adjustment member 122 to vary an amount of the adjustment member 122 that occupies the chamber 538. In other implementations, the adjustment member 122 may be positioned elsewhere on the handle 110, such as within fluid passageways of the handle 110 other than the chamber 538. In the illustrated implementation, the adjustment member 122 may be made to extend into the chamber 538 such than an end 562 of the adjustment member resides closely to an inlet 564 of the bore 540. As the adjustment member 122 is moved farther into the chamber 538 and the end 562 is moved farther into the inlet 564, the cross-sectional area of the inlet 564 and the amount of fluid flow out of the vent 120 decreases. The adjustment member 122 may also be positioned such that no part of the adjustment member 122 occupies a portion of the chamber 538. In such circumstances, the adjustment member 122 does not decrease the cross-sectional area of the inlet 564 of the bore 540. The adjustment member 122 may be positioned at any desired location within the chamber 538 and relative to the inlet 564 so as to provide a desired rate of movement of the piston 550 when it returns to an unactuated position by moving in the direction of arrow 139.

To return the piston 550 to an unactuated position, the user removes his or her finger from over the vent 120 to allow fluid flow out of the vent 120. With the adjustment member 122 positioned to decrease the cross-sectional area of the inlet 564 and to reduce the fluid flow out of the vent 120, the fluid pressure within the chamber 538 is relieved (or decreases) at relatively slower rate. The slower pressure decrease within the chamber 538 results in the piston 550 returning to an unactuated position at a correspondingly slower rate. If the end 562 of the adjustment member 122 is positioned farther from the inlet 564, then the cross-section area of the inlet 564 is reduced to a lesser extent (or not at all) and relatively more fluid flows out of the vent 120. Thus, when the user removes his or her finger from the vent 120, the piston 550 returns to an unactuated position at a relatively faster rate because the fluid pressure is relieved within the chamber 538 faster than when less fluid flows out of the vent 120.

In some circumstances, the adjustment member 122 may selectively increase and decrease the rate at which piston 550 is actuated. Generally, the adjustment member 122 may selectively increase or decrease the volume of the chamber 538 that is adjacent to the piston 550. As the adjustment member 122 is moved farther into and occupies more of the chamber 538, the volume of the chamber 538 that can be occupied by the fluid decreases. The user may cover the vent 120 with a finger to actuate the piston 550, resulting in a fluid pressure increase within the chamber 538. Because the volume of the chamber 538 is smaller as a result of the adjustment member 122, the fluid pressure within the chamber 538 increases at a relatively faster rate. When the adjustment member 122 occupies less of the chamber 538 (or none at all), the volume of the chamber 538 is relatively larger. Thus, when the vent 120 is occluded, the piston 550 is actuated at a relatively slower rate because the volume of the chamber 538 is relatively larger.

Figure 6:
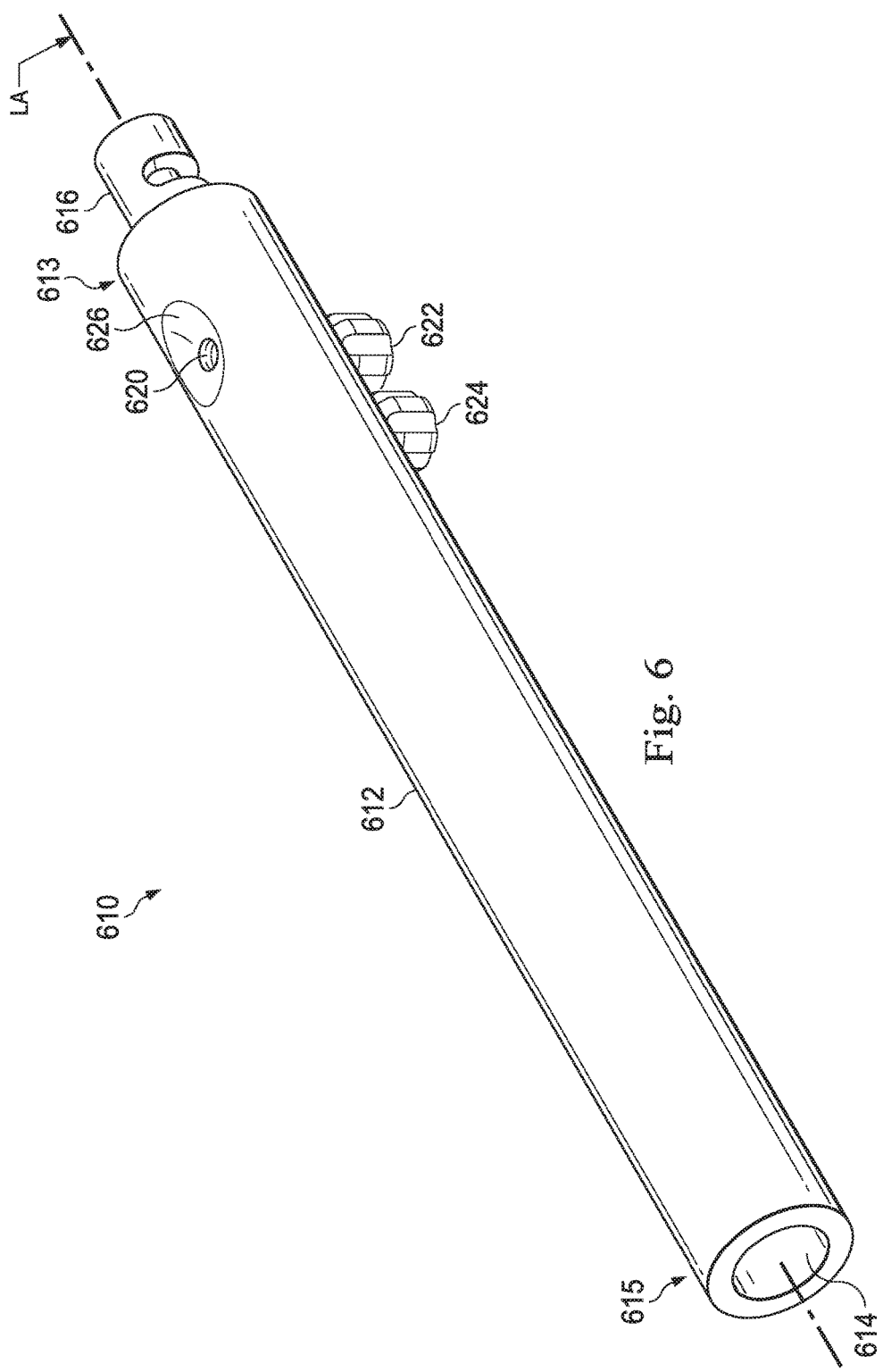
FIG. 6 is a perspective view of an example ophthalmic device handle showing the proximal end thereof.
Figure 7:
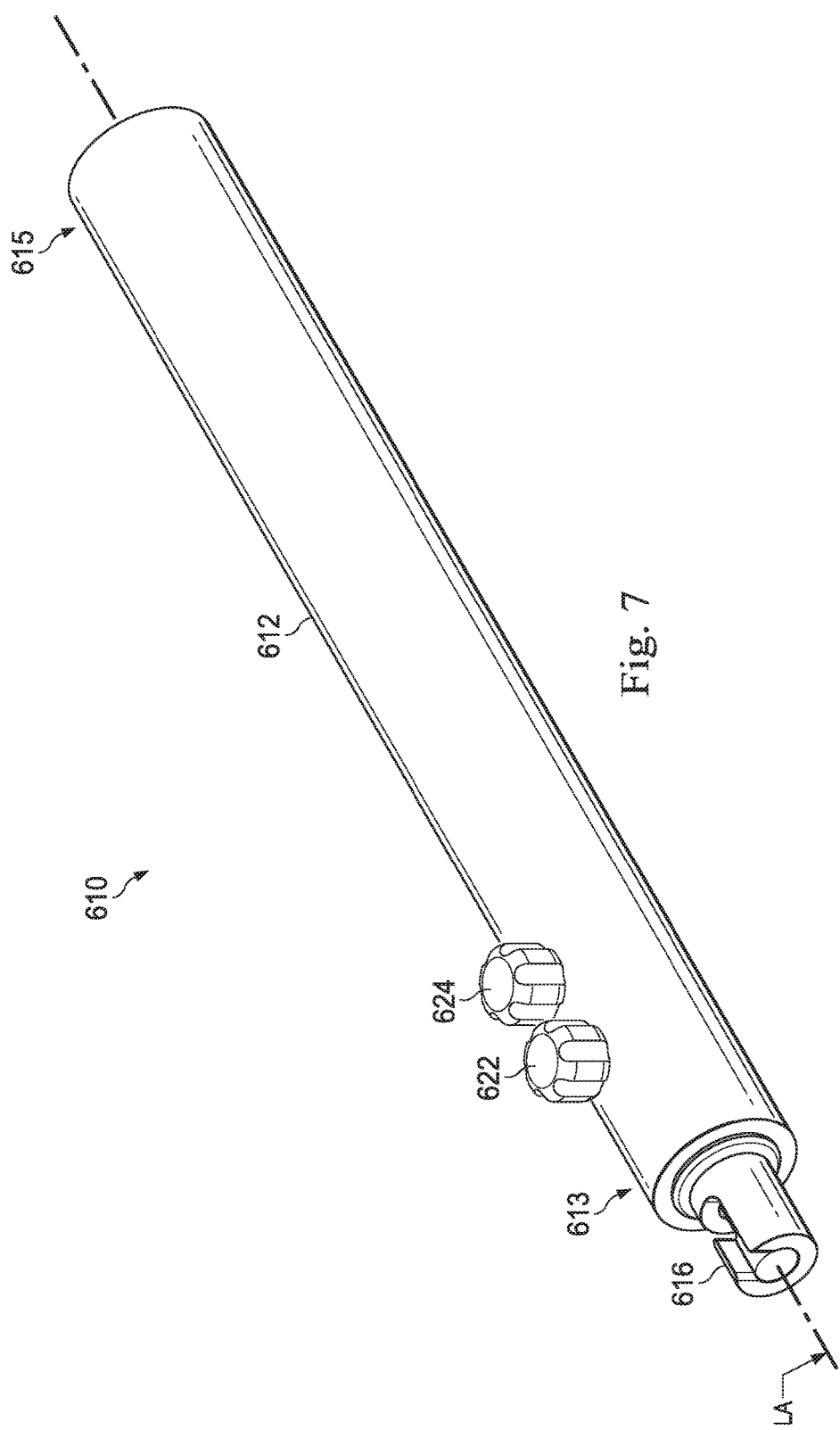
FIG. 7 is another perspective view of the ophthalmic device handle of FIG. 6 showing the distal end thereof.

FIGS. 6-9 illustrate another example ophthalmic device handle 610. FIGS. 6 and 7 are perspective views of the handle 610. A proximal portion 615 of the body 612 is shown in the foreground of FIG. 6. A distal portion 613 of the body 612 is shown in the foreground of FIG. 7. Relative to orientation of the handle 610 illustrated in FIG. 6, the handle 610 in FIG. 7 is rotated 180° about the longitudinal axis LA. FIGS. 8 and 9 are cross-sectional views of the handle 610.

The handle 610 may be implemented in a surgical system, such as surgical system 100 shown in FIG. 1. The handle 610 may be similar in many respects to the handle 110 described herein. The handle 610 includes a body 612. The body 612 is generally cylindrical and has a substantially constant diameter along its entire length. In other implementations, the body 612 may be variously sized and shaped. The size and shape of the body 612 may be selected so as to facilitate grasping by a user. The handle 610 may be removably coupled to and instrument, such as an instrument tip similar to the instrument tip 130 shown in FIG. 1, via a connector 616. The connector 616 and/or the instrument tip may be variously sized and shaped in different implementations to facilitate the desired connection between the two components.

The handle 610 may be in fluid communication with a fluid source similar to the fluid source 142 shown in FIG. 1. For example, any suitable conduit configured to carry a fluid may extend between the fluid source and the handle 610. The fluid conduit may be coupled to a port 611 of the handle 610, such as at a proximal portion 613. Fluid may flow continuously through various fluid passageways within the handle 610. The handle 610 includes a lumen 614 extending along a length thereof. The lumen 614 receives the fluid from the fluid source. While the example lumen 614 is shown to have a constant diameter, the scope of the disclosure is not so limited. Rather, in other implementations, the diameter of the lumen 614 may vary. Further, in other implementations, the lumen 614 may not be circular in cross-section. Rather, any desired shape and size of the lumen 614 may be selected. The length over which the lumen 614 extends within the body 612 may also be varied. As described with respect to the lumen 520 (FIG. 5), the length of the lumen 614 may be related to the length of the body 612 in varying proportions. For example, the lumen 614 may extend between about 1% and about 99%, between about 30% and about 90%, between about 40% and about 90%, greater than 50%, and other desired proportions relative to the length of the body 612. Lumen 614 fluidly communicates with lumen 930. Lumen 930 fluidly communicates with chamber 938. Thus, from the lumen 614, fluid may flow into the lumen 930 and the chamber 938. The chamber 938 is in fluid communication with vent 620. Therefore, fluid may enter the handle via port 611, flow through the handle 610 via lumens 614 and 930 and chamber 938, and exit the handle 610 via the vent 620.

When the vent 620 is occluded, such as when a user positions his or her finger over the vent 620, fluid pressure increases within the handle 610 because fluid flow out of the handle 610 is impeded. The fluid pressure within the chamber 938 exerts a force on the adjacent piston 950, as best seen in FIG. 9. With the vent 620 closed, fluid pressure sufficient to overcome the force of the biasing element 952 displaces the piston 950 in the direction of arrow 937, thereby compressing biasing member 952. As shown in FIGS. 8 and 9, the biasing element 952 may be a coil spring. However, the biasing element 952 may be any desired element operable to bias the piston 950 in a desired direction. While the example shown in FIGS. 8 and 9 show the piston 950 being linearly translatable distally when actuated, the piston 950 may be actuatable in different ways. For example, in other implementations, the piston 950 may be rotated, pivoted, and/or otherwise moved when actuated. The user actuates the instrument tip coupled to the handle 610 by occluding the vent 620, causing the fluid pressure within chamber 938 to displace the piston 950. When the vent 620 is no longer occluded, such as when the user removes his or her finger from the vent 620, fluid pressure within the handle 610 decreases as the fluid exits the handle 610 via vent 620. As a result, the piston 950 moves proximally in the direction of arrow 939 to an unactuated position. For example, the biasing element 952 urges the piston 950 in the proximal direction to the unactuated position. In turn, an instrument tip coupled to the handle 610 returns to an unactuated position The handle 610 may include a depression 626 on an exterior surface of the body 612. The depression 626 may surround the vent 620. The depression 626 may allow a user to quickly locate the vent 620 by tactilely feeling the depression 626 with his or her fingers. While the illustrated implementation includes a single vent 620 and a single depression 626, other implementations may include two or more vents and/or two or more depressions. The multiple vents and depressions may be proximate or spaced from one another. In such implementations, the user may position two or more fingers over the respective two or more vents to control an instrument tip coupled to the handle 610.

The handle 610 may also include adjustment members 622 and 624 that function similarly to the adjustment members 122 and 124, respectively, described above. In the illustrated implementation, the adjustment members 622 and 624 are disposed at the distal portion 615 of the body 612 and on an opposing side of the vent 620. However, the adjustment members 622 and 624 may be located along any desired radial extending from longitudinal axis LA. Further, in other implementations, one, the other, or both of the adjustment members 622 and 624 may be disposed at other locations of the handle 610. The size and shape of the adjustment members 622 and 624 may be selected, for example, to control the manner in which the piston 950 reacts to a given change in position of the adjustment members 622 and 624.

The adjustment member 624 may be a screw or other threaded component that may have a threaded engagement with bore 625. The adjustment member 624 may be advanced into the lumen 930 such that a distal end 627 of the adjustment member 624 is received within the slot 936. Further, an amount that the adjustment member 624 extends into the lumen 930 may be selected to be any desired amount. Similar to the adjustment member 124, described above, an amount the adjustment member 624 is made to extend into the lumen 930 controls the rate at which the piston 950 (and any coupled instrument tip) is actuated. The more the adjustment member 624 extends into the lumen 930 results in the piston 950 being actuated at a slower rate. Similarly, the less the adjustment member 624 extends into the lumen 930 results in the piston 950 being actuated at a faster rate.

The adjustment member 622 controls the rate at which the piston 950 (and any coupled instrument tip) returns to an unactuated position. The adjustment member 622 is movable within a bore 623 and extends into the chamber 938, as best shown in FIG. 9. The adjustment member 622 may have a threaded engagement with the bore 623. As the adjustment member 622 is moved further into the chamber 938, the cross-sectional area of the vent 620 decreases. The user may position the adjustment member 622 to alter an amount, if any, that the adjustment member 622 occupies the chamber 938 and affects the cross-sectional area of the vent 620. In a manner similar to that described above, as the amount by which adjustment member 622 extends into the chamber 938 and the vent 620, the lower the rate at which the piston 950 returns to an unactuated position. Conversely, the piston 950 returns to the unactuated position at a faster rate as the amount that the adjustment member 622 extends into the chamber 938 and the vent 620 decreases. As also described above, the position of the adjustment member 622 may also selectively increase or decrease the rate at which the piston 950 is actuated by impacting the volume of the chamber 938. When the adjustment member 622 occupies a greater volume within the chamber 938, the fluid pressure within the chamber 938 increases more quickly and the piston 950 is actuated at a relatively faster rate. When the adjustment member 622 occupies less of the chamber 938, the fluid pressure within the chamber 93 increases more slowly and the piston 950 is actuated at a relatively slower rate.

The adjustment member 622 may include a head 922, and the adjustment member 624 may include a head 924. A user may adjust the position of the adjustment members 622 and 624 using the heads 922 and 924, respectively, such as by rotating the heads 922 and 924 to move the adjustment members 622 and 624 correspondingly. The heads 922 and 924 may extend beyond an exterior surface of the handle 610. In the illustrated implementation, the heads 922 and 924 are enlarged and generally cylindrical. However, the heads 922 and 924 may have any shape or size. The heads 922 and 924 may also include grooves, knurling, and/or texturing to facilitate grasping by a user. Generally, the size and shape of the heads 924 and 922 may vary in different implementations so as to allow the user to quickly locate and rotate the heads 922 and 924 to adjust the position of the adjustment members 922 and 924.

Figure 10:
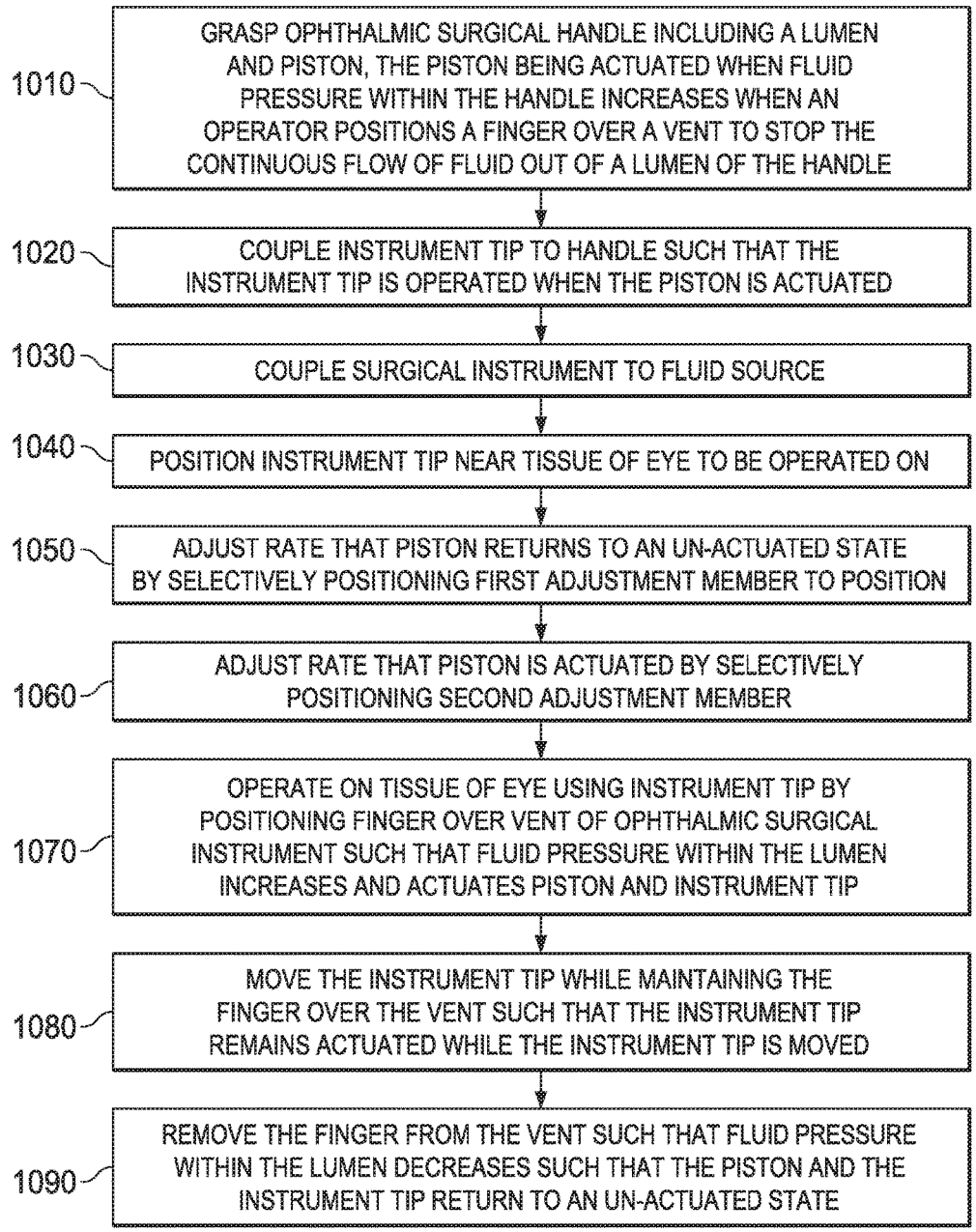
FIG. 10 is an example flowchart illustrating a method of performing an ophthalmic surgical procedure.

FIG. 10 illustrates a flowchart of an example method 1000 of performing an ophthalmic surgical procedure. As illustrated, the method 1000 includes a number of enumerated steps, but implementations of the method 1000 may include additional steps before, after, and in between the enumerated steps. In some implementations, one or more of the enumerated steps may be omitted or performed in a different order.

At step 1010, the method 1000 includes grasping an ophthalmic surgical handle having a lumen and a piston. The ophthalmic surgical instrument may be configured to permit continuous fluid flow through the lumen and out of a vent. The handle may be similar to any of the handles described herein. For example, the handle may be similar to the handle 110 shown in FIG. 5. The piston may be configured to be actuated when fluid pressure within the handle increases. The fluid pressure may increase when a user positions a finger over the vent to stop the continuous flow of fluid out of a lumen of the handle.

At step 1020, the method 1000 includes coupling an instrument tip to the handle, such as the instrument tip 130 being coupled to the handle 110, as shown in FIGS. 1 and 2. Together, the instrument tip and the handle may be described as ophthalmic surgical instrument. Actuation of the piston may operate the instrument tip (e.g., opening and closing jaws of a forceps, pivoting the blades of scissors, etc.) At step 1030, the method 1000 includes coupling the surgical instrument to a fluid source. For example, the handle may be fluidly coupled to the fluid source such that the fluid continuously flows through the lumen of the handle and out of the vent.

Figure 11:
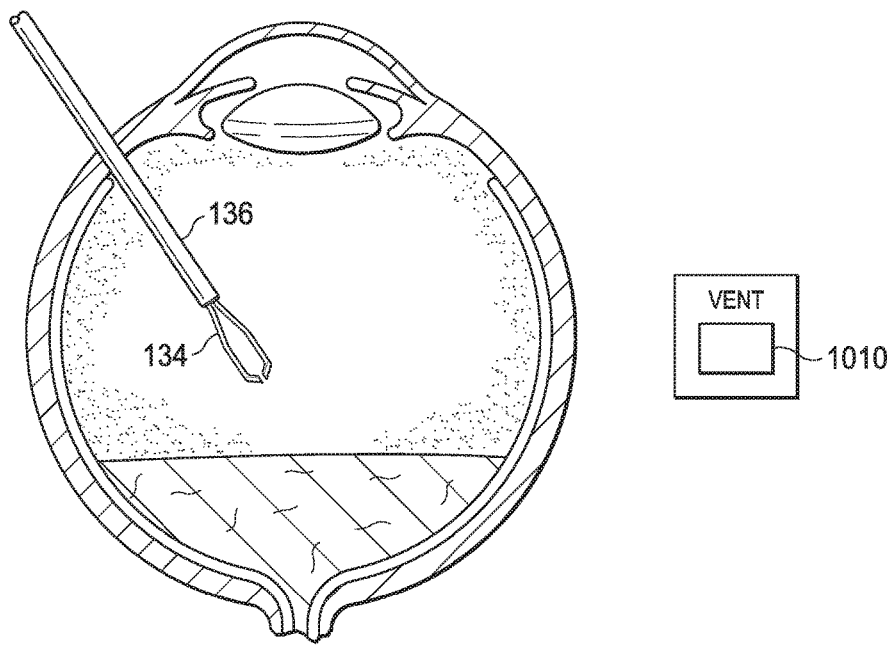
FIG. 11 shows an instrument tip in an unactuated position in situ in the eye.

At step 1040, the method 1000 includes positioning the ophthalmic surgical instrument so that an instrument tip of the ophthalmic surgical instrument is disposed near tissue of the eye to be operated on. The tissue may be in the anterior segment of the eye or posterior segment of the eye. The tissue may be on or near a surface of the eye. The target tissue may be within the globe of the eye. For example, to access an interior of the eye, the user may create one or more incisions in the sclera of the eye. The one or more incisions permit access to a posterior segment of the eye, such as the vitreous chamber. Various surgical devices, including an ophthalmic surgical instrument of a type described herein, an aspiration probe, a cutting probe, a vitrectomy probe, an illuminator, infusion line, as well as others, may be inserted into the vitreous chamber via the one or more incisions. The instrument tip may be inserted such that, for example, jaws of the instrument tip are positioned proximate to a tissue of the eye that the user intends to grasp. This is illustrated in FIG. 11 and shows a portion of the instrument tip (i.e., the actuation tube 136 and the jaws 134) near target anatomy within the eye. The jaws may be in an unactuated position as the vent of the handle is not occluded, allowing fluid to flow through the handle and out of the vent. The vent being unoccluded is indicated by the unshaded box 1010 in FIG. 11. For example, the user's finger may be positioned so as not to cover or only partially cover the vent.

At step 1050, the method 1000 includes adjusting the rate at which the piston returns to an unactuated position by selectively positioning an adjustment member, such as, for example, adjustment member 122 and 622, discussed above. For example, the surgeon may adjust the position of the adjustment member to alter the rate at which pressure within the handle is relieved and/or alter the fluid flow rate out of the handle.

At step 1060, the method 1000 includes adjusting the rate at which the piston is actuated by selectively positioning an adjustment member, such as, for example, adjustment member 124 and 624, described above. For example, the user may adjust the position of the adjustment member to selectively increase and decrease a rate at which is fluid pressure builds up within the body of the handle. For example, the position of the adjustment member may alter the rate at which the fluid pressure of a chamber proximate to the piston changes. Either, both, or neither of the steps 1050 and 1060 may be performed before, during, and/or after the other steps of the method 1000. For example, the position of one, the other, or both of the adjustment members may be adjusted before coupling the handle to the instrument tip, before coupling the surgical instrument and the fluid source, before/while/after the surgical instrument is positioned proximate to the target surgical tissue of the eye, before/while/after operating on tissue of the eye, etc.

At step 1070, the method 1000 includes operating on or otherwise manipulating the tissue of the eye using the instrument tip. The user may position a finger over the vent to reduce fluid flow from the vent such that fluid pressure within the lumen increases and actuates a piston in the handle, which acts on the instrument tip to act on the tissue of the eye. In the context of the handle 110, for example, the user may operate the instrument tip 130 by covering the vent 120 of the handle 110 such that fluid may no longer exit from an interior of the handle 110. The user may press a pad of a finger on the vent. Because fluid cannot exit via the vent, fluid pressure within the handle increases and actuates the piston and the instrument tip.

Figure 12:
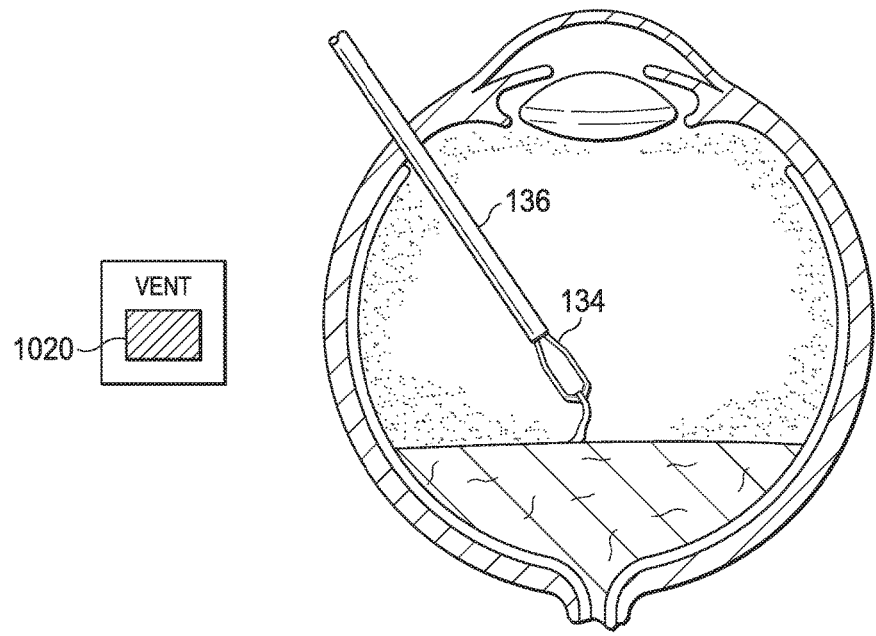
FIG. 12 shows an instrument tip in an actuated position in situ in the eye.

At step 1080, the method 1000 includes moving the instrument tip while the instrument tip remains in the actuated position. That is, the user may maintain the finger over the vent while moving the instrument tip. While the vent is covered, fluid flow out of the handle via the vent is impeded, and the piston and the instrument tip remain actuated. Step 1080 may occur in some surgical procedures, such as when a user uses the jaws of the instrument tip to grasp and peel tissue of the eye. Steps 1070 and 1080 are illustrated in FIG. 12. As indicated by the shaded box 1020, the vent is occluded. For example, the vent may be partially or completely covered by the user's finger. Under such circumstances, the actuation tube 136 is translated distally, urging the jaws 134 into an actuated position and gripping tissue within the eye. The instrument tip 134 may be moved while the jaws 134 continue to grip the tissue as the vent 120 remains covered. In other surgical procedures, such as, for example, when the instrument tip includes scissor blades, step 1080 may be omitted.

At step 1090, the method 1000 includes the removing the finger from the vent such that the piston and the instrument tip return to an unactuated position. For example, when the vent is uncovered, the fluid pressure within the handle decreases as fluid exits the vent. As a result, the piston and the instrument tip return to an unactuated position.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system, comprising:
   a body;
   a lumen formed in the body and configured to receive a pressurized fluid;
   a vent providing fluid communication between the lumen and an exterior the body, the vent adapted to be selectively occluded to alter a pressure condition within the lumen between a pressurized condition and a nonpressurized condition;
   a piston moveable to an actuated position in response to the pressurized condition and to an unactuated position in response to the nonpressurized condition; and
   a first adjustment component configured to selectively increase and decrease a rate at which the piston moves to an actuated position,
   wherein the first adjustment component is a threaded component received into a threaded bore formed in the body, the first adjustment component movable in a direction perpendicular to a longitudinal axis of the body to selectively increase and decrease a rate at which is fluid pressure builds up within the body.

2. The system of claim 1, further comprising a biasing component disposed within the body, the biasing component configured to bias the piston to the unactuated position.

3. The system of claim 1, further comprising a second adjustment component configured to selectively increase and decrease a rate at which the piston is returned to an unactuated position.

4. The system of claim 3, wherein the second adjustment component is a threaded component received into a threaded bore formed in the body, the second adjustment component moveable within a chamber adjacent to the piston to selectively increase and decrease a rate at which fluid pressure within the chamber is relieved.

5. The system of claim 1, further comprising a nozzle configured to be coupled to a fluid source.

6. The system of claim 1, wherein the body has a substantially constant outer cylindrical shape.

7. The system of claim 1, wherein the body comprises a plurality of sections, wherein the plurality of sections have different sizes.

8. The system of claim 1, further comprising a connector disposed at a distal portion of the body, wherein the connector is configured to interface with a removable instrument tip.

9. An ophthalmic surgical system, comprising:
a fluid source;
an ophthalmic device handle comprising:
　a body;
　a lumen formed in the body and in fluid communication with the fluid source;
　a vent formed in the body and providing fluid communication between the lumen and the exterior of the body, the vent adapted to be selectively occluded to alter a pressure condition within the lumen between a pressurized condition and an nonpressurized condition; and
　a piston at least partially disposed within the body and moveable into an actuated position in response to the pressurized condition and to an unactuated position in response to the nonpressurized condition; and
an instrument tip coupled to the ophthalmic device handle, the instrument tip movable into an actuated configuration in response to movement of the piston to an actuated position and moveable into an unactuated configuration in response to movement of the piston to the unactuated position, and further comprising at least one of:
a first component selectively movable within the body to selectively increase and decrease a rate at which the piston moves to an actuated position; and
a second component selectively movable within the body to selectively increase and decrease a rate at which the piston returns to an unactuated position.

10. The system of claim 9, wherein the fluid source is integrated into a surgical console.

11. The system of claim 9, wherein the instrument tip comprises at least one of forceps or scissors.

* * * * *